United States Patent [19]

Clemons

[11] Patent Number: 5,163,454
[45] Date of Patent: Nov. 17, 1992

[54] METHOD OF AND APPARATUS FOR MEASURING MOISTURE CONTENT OF A MOVING STREAM OF TOBACCO

[75] Inventor: Vernol G. Clemons, Walnut Cove, N.C.

[73] Assignee: R. J. Reynolds Tobacco Company, Winston-Salem, N.C.

[21] Appl. No.: 746,256

[22] Filed: Aug. 15, 1991

[51] Int. Cl.⁵ .............................. A24B 3/04
[52] U.S. Cl. .................. 131/302; 131/304; 131/905; 73/73
[58] Field of Search .............. 131/84.1, 84.3, 304, 131/306, 300, 302, 904, 905; 73/73-77

[56] References Cited

U.S. PATENT DOCUMENTS 3,974,839 8/1976 Wochnowski et al. ............ 131/304
4,856,539 8/1989 Lorenzen ....................... 131/84.1 X
5,060,664 10/1991 Siems et al. ....................... 131/84.1

Primary Examiner—Vincent Millin
Assistant Examiner—J. Doyle
Attorney, Agent, or Firm—Grover M. Myers; George C. Myers, Jr.

[57] ABSTRACT

A method of and an apparatus for accurately measuring the moisture content of a moving bed of a product, such as strip tobacco, are disclosed. As the bed of tobacco is conveyed by a perforated or porous conveyor, a flow of air is directed upwardly through the conveyor and into the bed of tobacco. The air flow agitates and homogenizes the tobacco to provide a localized area of the bed of tobacco that has a substantially uniform moisture content from top to bottom. A moisture sensor located downstream of the air flow measures the moisture content of the agitated portion of the tobacco bed.

31 Claims, 1 Drawing Sheet

METHOD OF AND APPARATUS FOR MEASURING MOISTURE CONTENT OF A MOVING STREAM OF TOBACCO

FIELD OF THE INVENTION

The present invention relates to improvements in apparatus and methods for performing an in-line measurement of the moisture content of tobacco, especially for measuring the moisture content of strip tobacco conveyed on a drying line.

BACKGROUND OF THE INVENTION

The manufacture of cigarettes and other smoking articles requires the storage of tobacco strip used for the cut tobacco filler for periods of up to 24 months at a moisture content within a desired range. If the tobacco is stored with a high moisture content, i.e., too wet, a preservation problem arises with the possibility that the tobacco will mildew or rot. If the tobacco is stored with a low moisture content, i.e., too dry, it will not age properly, and the resultant product will be subject to excessive breakage during subsequent processing. Typical desired moisture contents are 12.5 percent by weight for flue cured tobacco strip and 13 percent by weight for burley tobacco strip.

Prior to the aging of tobacco during the storage period, the tobacco leaf is cut and formed as a bed or stream on a conveyor system. The conveyor system moves the tobacco stream through various processing stages, including a drying stage, then to a cooling stage where the moisture content is measured, typically by an infrared or near-infrared moisture meter, and then to a reordering stage where the moisture content is finally adjusted to provide the desired moisture content. The drying of the tobacco is performed by blowing air in both updraft and downdraft directions. This results in a compacting or densification of the moving stream of tobacco strip and a slight drying of the tobacco at the upper or exposed surface of the tobacco stream. It is therefore difficult to obtain accurate moisture readings for such a stream of densified tobacco. The standard deviation of moisture content measurement tends to be relatively large and the average moisture content measured by the moisture meter tends to be lower than actual because of the densification and non-uniformity of moisture content from top to bottom of the bed of tobacco strip.

The present invention is directed to overcoming the undesirable effects of measuring the moisture content of a densified stream of tobacco.

SUMMARY OF THE INVENTION

The present invention is directed to a method and apparatus for measuring the moisture content of tobacco strip with improved accuracy by reducing the densification of the tobacco at the point of measurement. This is achieved by providing a bed of strip tobacco on a porous or perforated apron of a process conveyor, drying the tobacco to a desired degree, agitating and blending a longitudinal portion of the bed of tobacco by flowing air upwardly through the perforated apron and into the tobacco, then interrupting the flow of air such that the tobacco strip will fall by gravity and settle back onto the conveyor apron in the form of a longitudinal ridge of tobacco having a more uniform moisture content from top to bottom, and then measuring the moisture content of the tobacco in the ridge.

The apparatus of the invention which performs this process is comprised of a conveyor apron which is perforated and on which the tobacco strip is conveyed. The apron comprises a plurality of perforated plates supported by a plurality of apron girths attached to the underside of the plates essentially transverse to the direction of conveyance. A compressed air pipe having a closed end portion with a plurality of radial holes supplies compressed air into the channel formed between two adjacent girths. The compressed air passes through the perforated plate between the adjacent girths and fluffs up and blends or mixes the tobacco in a localized area by agitating and fluidizing the tobacco. To aid in confining the area of fluffed up tobacco and to insure adequate mixing, a mixing chamber is located just above the apron and tobacco bed.

The passage of each girth over the compressed air pipe interrupts the upward flow of air through the apron between the downstream pair of girths permitting the tobacco to fall back onto the apron. Thus, a continuous longitudinal ridge of thoroughly blended tobacco strip is formed in the tobacco bed. Located downstream of the mixing chamber, a moisture sensor in the form of a conventional infrared or near-infrared meter measures the moisture content in the tobacco ridge. Such method and apparatus reduces the standard deviation of the moisture content measurement results in a measured average value of moisture content that is closer to actual moisture content. Thus, a more accurate measurement of the moisture content is possible with the apparatus and method of the present invention.

With the foregoing and other advantages and feature of the present invention that will become hereinafter apparent, the nature of the invention will be more clearly understood by reference to the following detailed description of the invention, the appended claims and to the several views illustrated in the attached drawings.

DETAILED DESCRIPTION OF THE INVENTION

Figure 1:
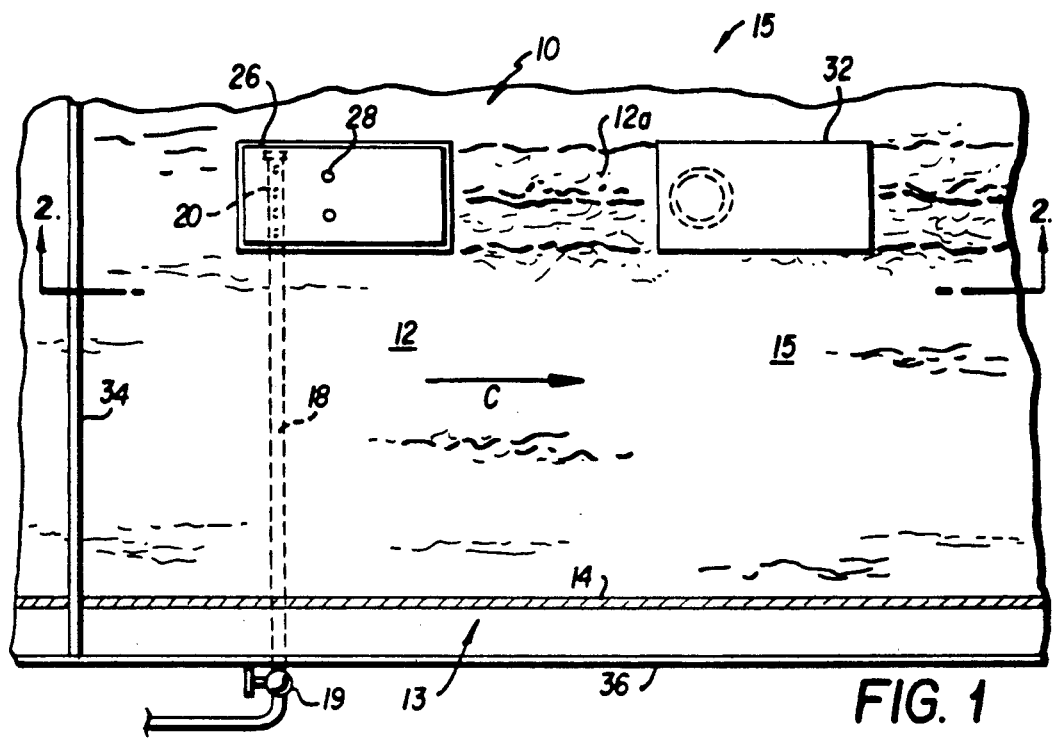
FIG. 1 is a top plan view of an apparatus according to the present invention.
Figure 2:
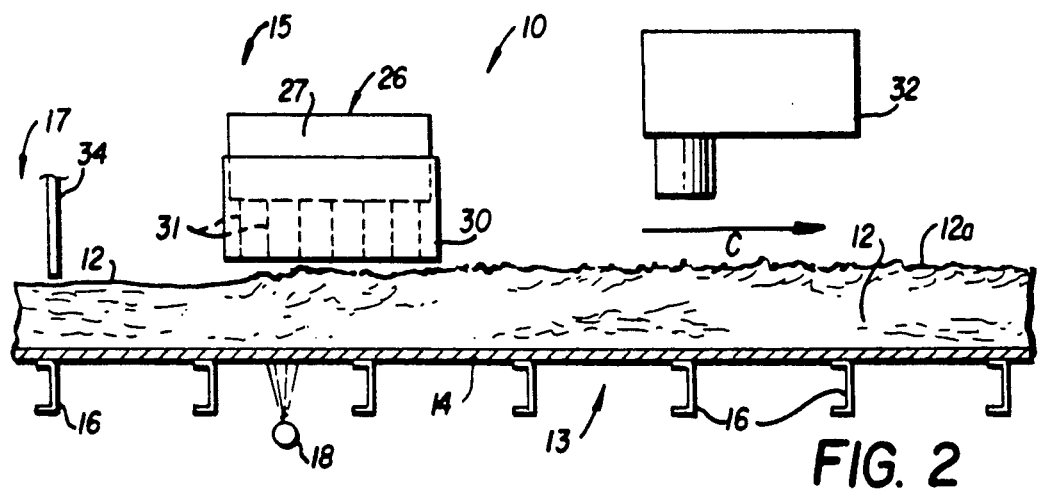
FIG. 2 is a side elevation view of the apparatus of the invention and the tobacco bed taken along section 2—2 of FIG. 1.

Referring now in detail to the drawings wherein like parts are designated by like reference numerals throughout, there is illustrated in FIGS. 1 and 2 an apparatus 10 embodying the present invention for measuring the moisture content of a moving stream of tobacco.

As shown in FIGS. 1 and 2, a bed of strip tobacco 12 or other smokable material, the moisture content of which is to be measured, is conveyed along a path of travel by a conveyor 13 comprising a dryer apron 14 constructed of a plurality of perforated plates connected together to form the conveyor surface. Attached to the underside of the dryer apron 14 and movable therewith is a plurality of apron girths or beams 16 which support the apron 14. The apron girths 16 are aligned substantially parallel to one another and transversely of the direction of tobacco conveyance, as indicated by the arrow C in FIGS. 1 and 2. Apparatus 10 also includes a compressed air pipe 18 arranged in a stationary position beneath the dryer apron 14. Pipe 18 is positioned sufficiently below the apron girths 16 so as to provide clearance for the passage of the girths as the dryer apron 14 moves along in the direction of arrow C. Compressed air flow in pipe 18 is regulated by a gate valve 19.

Figure 3:
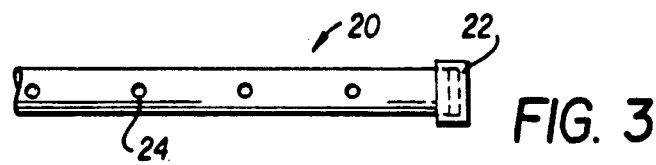
FIG. 3 is a fragmentary top plan view of an end portion of the compressed air pipe used in the apparatus of the present invention.

As shown in FIG. 3, an end portion 20 of the compressed air pipe 18 is fitted with an end plug 22 and has a plurality of aligned air exit holes 24 provided radially in the pipe. Located above the dryer apron 14 over the position of the pipe end portion 20 is a mixing chamber 26 comprising a metal hood 27 having a plurality of air relief holes 28 in the upper surface thereof. Mixing chamber 26 is an essentially rectangular enclosure, open at the bottom to which is attached a skirt 30 comprising a depending flexible sheet with vertical slits 31. The flexible skirt 30 extends downwardly from the lowermost edge of the hood 27 to a position in close proximity to the upper surface of the tobacco bed 12 for a purpose to be hereinafter described.

Located downstream of mixing chamber 26 and aligned with the mixing chamber 26 in the conveyance direction C is a moisture meter 32, which is preferably of the infrared or near-infrared type. The apparatus shown in this embodiment is located in the cooling room air lock 15 of a tobacco drying line downstream of the dryer section 17. The cooling room air lock 15 is delimited in the illustrated embodiment by the air lock wall 34 and the sidewall 36 of the dryer.

Conveying systems and drying lines for tobacco vary in design, construction and operation such that the moisture content of the tobacco in the transverse direction of the conveyor (i.e., as viewed at a right angle to the direction of tobacco conveyance shown by the arrow C in FIG. 1), may not be uniform. Moisture content data taken at spaced points along a plane transverse to the conveyance direction C can be used to establish a moisture content profile of a particular drying line. Based on such a profile, the optimum or preferred transverse location of the apparatus 10 and moisture meter 32 can be determined. Since storage of tobacco in a "too wet" condition, i.e., a moisture content above that desired, is considered more detrimental than storage in a "too dry" condition, i.e., a moisture content below that desired, the preferred or optimum location of the apparatus 10 and moisture meter 32 in the transverse direction of conveyance is at that point on the moisture content profile of the particular drying line corresponding to the highest moisture content. Of course, if the moisture content profile of a drying line is substantially uniform, the transverse positioning of the apparatus will be dictated by other considerations, such as convenience, access and the like.

The present invention also contemplates that in the practice of the invention, the apparatus 10 and moisture meter 32 may be mounted on a transversely movable support within the cooling room air lock 15 of the drying line to provide for varying the transverse position of the apparatus 10 and moisture meter 32 to coincide with the preferred transverse location as determined above. Such arrangement is advantageous, for example, should modifications in the drying line, the passage of time or other factors result in variations in the moisture content profile of the particular drying line.

The moisture meter 32 is preferably an infrared moisture sensor manufactured by Infrared Engineering of Waltham, Mass. under the model designations IE512 or TM55. A MICROQUAD 8000 infrared moisture sensor manufactured by Moisture Systems, Inc. of Hopkinton, Mass. may also be used. The dryer apron 14 is typically made of galvanized steel plate having a plurality of perforations of about ⅛ inch in diameter and about 30 perforations per square inch. The tobacco bed 12 may vary in depth from about 1 inch to about 4 inches, but is preferably about 3 to 3½ inches. In one operative embodiment, the mixing hood 27 of the mixing chamber 26 is about 12 inches long by 6 inches wide and 5 inches high with the lowermost edge of skirt 30 extending downwardly from the bottom edge of the hood 27 about 6 inches. Mixing chamber 26 is mounted above the conveyor 13 such that the bottom of skirt 30 is located about 3 inches above the dryer apron 14 in close proximity to the uppermost surface of the tobacco bed. The compressed air pipe 18 is preferably ½ inch O.D. having preferably four holes of ¼ inch diameter located about 1 inch apart in the pipe end portion 20. Compressed air is supplied to pipe 18 at a pressure typically in the range of about 5–70 psig, and preferably in the range of about 30–50 psig.

The apparatus 10 operates as follows. The bed of tobacco 12 is conveyed on dryer apron 14 by conveyor 13 from the dryer section 17 to the cooling room air lock 15. As the bed 12 passes over the compressed air pipe end portion 20, a stream of compressed air passes up through the perforated plates of dryer apron 14 and into the bed 12 of strip tobacco. The agitation of the tobacco by the air flow results in a fluidization or fluffing up of the tobacco into mixing chamber 26. The adjacent apron girths 16 longitudinally confine the air flow to the space between the adjacent girths so that as the upstream girth of a pair travels past the end portion 20 of the air pipe 18, the air flow between the girths is interrupted thereby permitting the tobacco within the mixing chamber 26 to fall or resettle by gravity onto the apron 14. The air agitation of the strip tobacco mixes and homogenizes a narrow section 12a of the tobacco bed 12, the narrow section having a width less than the width of the bed 12, as shown in FIGS. 1 and 2, eliminates the densification of the bed and thereby provides a section or ridge 12a of the bed with tobacco having a more uniform moisture content from top to bottom of the bed. As a result of the fluidization and resettling of the tobacco strip, a slight ridge 12a is formed in the bed 12, having a width substantially corresponding to the width of the mixing chamber 26. Formation of the ridge is similar in appearance to the burro by a mole tunnelling underground. The ridge 12a passes beneath moisture meter 32 where the moisture content of the tobacco is measured.

The method of the invention comprises the steps of providing a bed of tobacco, passing compressed air upwardly through the tobacco to agitate the tobacco and thereby fluidize and homogenize the tobacco, interrupting the flow of compressed air thereby permitting the tobacco to resettle by gravity onto the bed, and measuring the moisture content of the homogenized tobacco.

As used herein, the terms "agitate," "mix," "blend," "homogenize" and like terms are intended to mean that the product bed, such as a bed of tobacco strip, through which the flow of compressed air is directed is caused to undergo sufficient relative movement among the individual particles, strips or fibers of the product bed to redistribute the product in such a way that the moisture content of the product is more uniform through the thickness of the bed in that portion of the bed where the moisture measurement is made.

It will be appreciated by those skilled in the art that the present invention could be utilized in other environments and applications for obtaining more accurate measurements of moisture content of a product where densification or the non-homogeneous nature of the product may result in erroneous measurements of moisture content. For example, the invention could be used in the measurement of the moisture content of a stationary or moving bed of cut tobacco filler. It could also be used downstream of the reordering stage of the tobacco strip drying line to check the final moisture content of the strip tobacco before it is packed and stored. In the case of a stationary bed of a product, such as cut filler, the air pipe and moisture sensor could be moved relative to the bed or point-by-point measurements could be made by opening and closing the air gate valve 19 in the pipe 18. Other applications will be apparent to those skilled in the art in view of the invention disclosed herein.

Although a certain presently preferred embodiment of the invention has been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. Apparatus for measuring the moisture content of a bed of a product comprising:
    means for agitating a portion of the bed of the product, said agitated portion having a width less than the width of the bed;
    means for interrupting the agitation of the portion of the bed of the product, thereby permitting the product to resettle onto the bed; and
    means positionable over the agitated portion of the bed for measuring the moisture content of the agitated portion of the bed.

2. Apparatus according to claim 1, wherein said product is tobacco.

3. Apparatus according to claim 1, wherein said product is strip tobacco or cut filler.

4. Apparatus according to claim 1, wherein said agitating means comprises means for supplying a flow of air into the portion of the bed to be agitated.

5. Apparatus according to claim 1, including means for conveying the product bed along a path of travel, said conveying means comprising a perforated or porous apron and means located beneath said conveying means for supplying a flow of air through said apron into the portion of the bed to be agitated.

6. A method of measuring the moisture content of bed of a product comprising the steps of:
    agitating a portion of the product bed to homogenize such portion of the product bed, said portion having a width less than the width of the bed; and
    measuring the moisture content of the homogenized portion of the product bed.

7. Apparatus according to claim 1, wherein the width of said agitated portion is at least as great as the width of the moisture content measuring means.

8. Apparatus according to claim 1, wherein the agitated portion of the bed which has resettled onto the bed is in the form of a narrow ridge.

9. Apparatus according to claim 8, wherein the agitated portion of the bed which has resettled onto the bed is in the form of a narrow ridge.

10. Apparatus for measuring the moisture content of a bed of a product comprising:
    means for conveying the product bed along a path of travel, said conveying means comprising a perforated or porous apron and means located beneath said conveying means for supplying a flow of air through said apron into the portion of the bed to be agitated;
    means for agitating a portion of the bed of the product;
    means for interrupting the agitation of the portion of the bed of the product, thereby permitting the product to resettle onto the bed, said interrupting means comprising a plurality of apron girths mounted in spaced, supporting relation to said apron in a direction transverse to the path of travel of the conveyor means; and
    means positionable over the agitated portion of the bed for measuring the moisture content of the agitated portion of the bed.

11. Apparatus for measuring the moisture content of a bed of product comprising:
    means for agitating a portion of the bed of the product;
    means for confining the agitated product, said confining means comprising a mixing chamber disposed above the product bed, said mixing chamber having a flexible skirt extending toward and terminating in close proximity to said product bed;
    means for interrupting the agitation of the portion of the bed of the product, thereby permitting the product to resettle onto the bed; and
    means positionable over the agitated portion of the bed for measuring the moisture content of the agitated portion of the bed.

12. Apparatus according to claim 1, wherein said sensor means comprises an infrared or near-infrared moisture sensor.

13. Apparatus for measuring the moisture content of a bed of tobacco comprising:
    a conveyor having a perforated or porous apron for conveying the bed of tobacco along a path of travel;
    means for agitating a portion of the bed of tobacco, said agitating means comprising means disposed beneath the apron of the conveyor for supplying a flow of air through the apron and into the portion of the bed of tobacco to be agitated and means disposed above the bed of tobacco and the air flow supplying means for confining the agitated tobacco;
    means for interrupting the agitation of the portion of the bed of tobacco, thereby permitting the tobacco to resettle onto the bed, said interrupting means comprising a plurality of apron girths mounted to the underside of the apron transfersely of the path of travel for interrupting the flow of air to the agitated portion of the bed; and
    means positionable over the agitated portion of the bed for measuring the moisture content of the agitated portion of the bed.

14. Apparatus for measuring the moisture content of a moving bed of tobacco comprising:
- means for conveying the bed of tobacco along a path of travel, said conveying means having an apron supporting the bed of tobacco;
- air flow means disposed beneath the apron for supplying a flow of air through the apron and into the bed of tobacco to agitate and homogenize a portion of the bed of tobacco as it passes over the air flow means, said agitated portion having a width less than the width of the bed;
- means disposed above the bed of tobacco and downstream of the air flow means for measuring the moisture content of the agitated portion of the bed of tobacco.

15. Apparatus according to claim 14, wherein said tobacco is strip tobacco or cut filler.

16. Apparatus according to claim 14, wherein the agitated portion of the bed which has resettled onto the bed is in the form of a narrow ridge.

17. Apparatus for measuring the moisture content of a moving bed of tobacco comprising:
- means for conveying the bed of tobacco along a path of travel, said conveying means having an apron supporting the bed of tobacco;
- air flow means disposed beneath the apron for supplying a flow of air through the apron and into the bed of tobacco to agitate and homogenize a portion of the bed of tobacco as it passes over the air flow means;
- means disposed above the bed of tobacco and downstream of the air flow means for measuring the moisture content of the agitated portion of the bed of tobacco; and
- mixing chamber means disposed above the bed of tobacco and the air flow means for confining the agitated portion of the bed of tobacco, said mixing chamber means having a flexible skirt extending into close proximity to the bed of tobacco.

18. The method according to claim 6, wherein the product is tobacco.

19. A method according to claim 6, wherein the width of said homogenized portion in said agitating step is at least as great as the width of a device for performing said moisture content measuring step.

20. A method according to claim 6, wherein the homogenized portion is in the form of a narrow ridge.

21. The method according to claim 18, wherein said agitating step comprises the step of flowing air into the tobacco bed.

22. The method according to claim 21, including the step of conveying the bed of tobacco along a path of travel on a conveyor and flowing air through the conveyor and into the tobacco bed.

23. The method according to claim 22, including the step of confining the agitated tobacco in a mixing chamber located above the bed of tobacco.

24. A method of measuring the moisture content of a bed of tobacco comprising the steps of:
- conveying the bed of tobacco along a path of travel on a conveyor;
- agitating, by flowing air through the conveyor and into the tobacco bed, a portion of the product bed to homogenize such portion of the tobacco bed;
- determining the moisture content of the tobacco bed at a plurality of spaced points in a direction transverse to the direction of the conveyance of the tobacco bed to establish a moisture content profile of the tobacco bed; and
- performing the agitating and measuring steps at a transverse location of the bed selected from the moisture content profile.

25. The method according to claim 23, including the step of interrupting the flow of air into the portion of the tobacco bed.

26. The method according to claim 24, wherein the selected transverse location is at the point on the moisture content profile corresponding to the highest moisture content.

27. A method of measuring the moisture content of a bed of a product comprising the steps of:
- conveying the product bed in a first direction;
- determining the moisture content of the product bed at a plurality of spaced points in a second direction transverse to the first direction to establish a moisture content profile of the product bed;
- agitating a portion of the product bed to homogenize such portion of the product bed at a location in said second direction selected from the moisture content profile; and
- measuring the moisture content of the homogenized portion of the product bed.

28. The method according to claim 27, wherein the product is tobacco.

29. The method according to claim 27, wherein the selected location is at the point on the moisture content profile corresponding to the highest moisture content.

30. A method according to claim 27, wherein the width of said homogenized portion in said agitating step is at least as great as the width of a device for performing said moisture content measuring steps.

31. A method according to claim 27, wherein the homogenized portion is in the form of a narrow ridge.

* * * * *